(12) United States Patent
Frye-Mason et al.

(10) Patent No.: US 6,772,513 B1
(45) Date of Patent: Aug. 10, 2004

(54) METHOD FOR MAKING ELECTRO-FLUIDIC CONNECTIONS IN MICROFLUIDIC DEVICES

(75) Inventors: Gregory C. Frye-Mason, Cedar Crest, NM (US); David Martinez, Albuquerque, NM (US); Ronald P. Manginell, Albuquerque, NM (US); Edwin J. Heller, Albuquerque, NM (US); Rajen Chanchani, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 33 days.

(21) Appl. No.: 10/184,782

(22) Filed: Jun. 27, 2002

(51) Int. Cl.[7] ................................................ H25K 3/34
(52) U.S. Cl. .............................. 29/840; 29/825; 29/832; 137/597
(58) Field of Search .......................... 29/825, 832, 840, 29/841; 137/597

(56) References Cited

U.S. PATENT DOCUMENTS

| | | | |
|---|---|---|---|
| 5,690,763 A | | 11/1997 | Ashmead et al. |
| 6,076,406 A | * | 6/2000 | Blair et al. .................... 73/590 |
| 6,171,378 B1 | | 1/2001 | Manginell et al. |
| 6,251,188 B1 | * | 6/2001 | Hashimoto et al. ......... 118/715 |

OTHER PUBLICATIONS

A fFexible Package and Interconnects for Microfluidic Systems by W Bennett et al, a Paper at the International Symposium of Biomedical Opics, San Jose, CA Jan. 23–29, 1999.*

Field Effect Flow Control in a Polydimethylsiloxane–based Microfluidic System by J.S. Buch et al, Electrophoresis, 2001, 22 3902–3907.*

Benavides, eta l., "Method of Packaging and Assembling Electro–Microfluidic Devices", Patent application No. 09/790,305, filed Feb. 21, 2001.

Gray, et al., "Novel interconnection technologies for integrated microfluidic systems," *Sensors and Actuators 77*, 57 (1999).

Koch, et al., "Micromachined chemical reaction system," *Sensors and Actuators 74*, 207 (1999).

Frye–Mason, et al., "Hand–Held Miniature Chemical Analysis System (uChemLab) for Detection of Trace Concentrations of Gas Phase Analytes," *Micro Total Analysis Systems 2000*, 229 (2000).

Martin et al., "Gas Sensing with Acoustic Devices" in *Proc. IEEE Ultrasonics Symposium*, 423 (1996).

* cited by examiner

*Primary Examiner*—Carl J. Arbes
(74) *Attorney, Agent, or Firm*—Kevin W. Bieg

(57) ABSTRACT

A method for forming electro-fluidic interconnections in microfluidic devices comprises forming an electrical connection between matching bond pads on a die containing an active electrical element and a microfluidic substrate and forming a fluidic seal ring that circumscribes the active electrical element and a fluidic feedthrough. Preferably, the electrical connection and the seal ring are formed in a single bonding step. The simple method is particularly useful for chemical microanalytical systems wherein a plurality of microanalytical components, such as a chemical preconcentrator, a gas chromatography column, and a surface acoustic wave detector, are fluidically interconnected on a hybrid microfluidic substrate having electrical connection to external support electronics.

20 Claims, 6 Drawing Sheets

US 6,772,513 B1

METHOD FOR MAKING ELECTRO-FLUIDIC CONNECTIONS IN MICROFLUIDIC DEVICES

STATEMENT OF GOVERNMENT INTEREST

This invention was made with Government support under contract no. DE-AC04-94AL85000 awarded by the U. S. Department of Energy to Sandia Corporation. The Government has certain rights in the invention.

FIELD OF THE INVENTION

The present invention relates to packaging of microfluidic devices and, more particularly, to a method for making electro-fluidic connections in microfluidic devices.

BACKGROUND OF THE INVENTION

Chemical microanalytical systems, also known as "chemical laboratories on a chip," offer the promise of high analytical performance in systems that are small, consume low power, and have low manufacturing and operating costs. Such microanalytical systems require the manipulation of fluids for sample handling, mixing, separation, and detection of analytes. The fluid may be a gas, liquid, or a supercritical fluid. One of the major challenges for making reliable, robust, and low cost microanalytical systems is the assembly of multiple microanalytical components that require both electrical connections and leak free fluidic connections. In some cases, integration can be used to fabricate the microanalytical components and make the connections on a single substrate. However, the many different fabrication processes, chemically selective materials, and dimensions for the various microanalytical components generally favors independently fabricating the component dies and then assembling them together in a hybrid structure. Simple and reliable methods for performing this electrical and fluidic assembly are necessary.

The present invention provides a method for making the electrical and fluidic connections between a microfluidic substrate and a plurality of individual microanalytical components that require fluid flow and comprise active electrical elements. The method is simple and can be used with any microfluidic device wherein reliable fluidic and electrical connections are required.

SUMMARY OF THE INVENTION

The present invention is directed to a method for forming an electro-fluidic connection from a microfluidic substrate to a die having at least one active electrical element thereon, comprising forming at least one bond pad on the die that is electrically connected to the at least one active electrical element; forming a seal ring on the die around the outside of the at least one bond pad and the at least one active electrical element; forming at least one matching bond pad on the microfluidic substrate for connection to support electronics; forming a matching seal ring on the microfluidic substrate around the outside of at least one fluidic via hole; bonding the at least one bond pad to the at least one matching bond pad with a conductive sealant to form electrical connection from the microfluidic substrate to the active electrical element; and bonding the seal ring to the matching seal ring with a sealant to form a fluidic seal around the at least one active electrical element and the at least one fluidic via hole. Alternative methods for forming the electro-fluidic connection comprise forming an insulating seal ring on the inside of the electrical bond pads and on the outside of the at least one active electrical element.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

FIG. 3 is a schematic illustration of a die for a chemical preconcentrator to be bonded to a microfluidic substrate.

FIG. 5 is a schematic illustration of a die for a surface acoustic wave (SAW) detector to be bonded to a microfluidic substrate.

FIG. 6 shows photographs of a low-temperature cofired ceramic (LTCC) substrate.

DETAILED DESCRIPTION OF THE INVENTION

Figure 1:
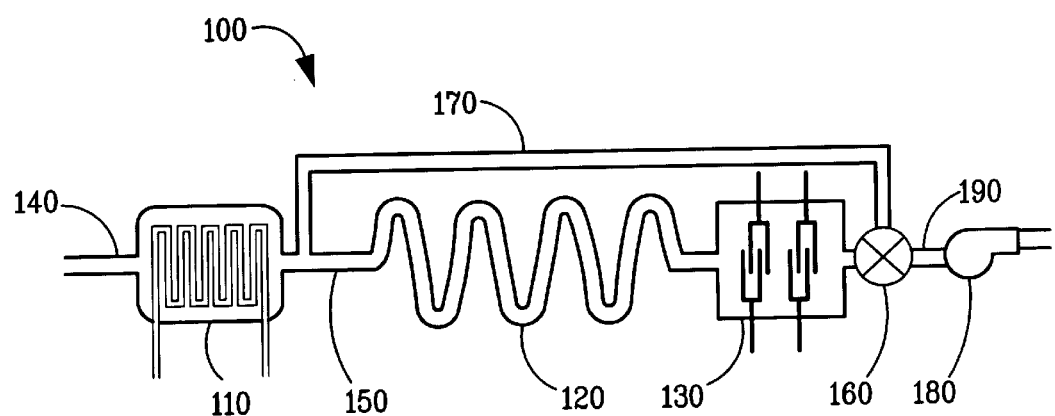
FIG. 1 is a schematic illustration of a typical microanalytical system.

Referring to FIG. 1, there is shown a schematic illustration of a typical microanalytical system 100 comprising a chemical preconcentrator 110, a gas chromatography (GC) column 120, and a surface acoustic wave (SAW) detector 130 as the microanalytical components. The preconcentrator 110 can use a thermally isolated membrane with an absorbent layer formed thereon to collect and concentrate target analytes from a fluid sample passing over the membrane. An integral resistive heater can provide rapid and low power heating of the membrane to rapidly desorb the collected analytes and provide a concentrated chemical pulse to the GC column 120. The GC column 120 can comprise a temperature-controlled high aspect ratio channel coated with a thin stationary phase material for separation of the desorbed analytes. The SAW detector 130 can use chemically selective coatings on the delay path between two interdigital transducers for high sensitivity detection of the separated analytes.

Electrical connections (not shown) are required from the active electrical elements of these microanalytical components to support electronics, such as the temperature control circuitry for the preconcentrator 110 and GC column 120 and the A-to-D converters for measuring the output of the SAW detector 130. Fluidic connections are required between the microanalytical components and from the microanalytical components to the external environment. A sample inlet 140 provides for flow of the fluid sample into the preconcentrator. An analysis channel 150 fluidically connects the cascaded microanalytical components. A 3-way valve 160 enables the fluid to bypass the GC column 120 through a bypass channel 170 during sample collection. A vacuum pump 180 can be attached to the valve 160 for removal of the effluent through an outlet 190 and for generation of the pressure drop required to achieve sufficient fluid flow through the microanalytical system 100.

Figure 2:
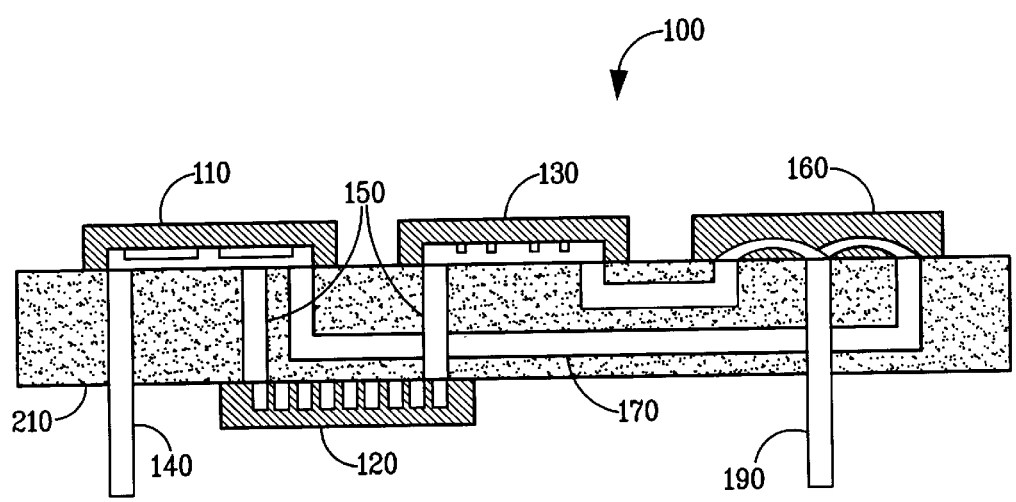
FIG. 2 is a cross-sectional schematic illustration of the typical microanalytical system assembled in a hybrid structure.

In FIG. 2 is shown a cross-sectional schematic illustration of the microanalytical system 100 comprising a hybrid structure wherein the individual microanalytical component dies are separately fabricated and assembled on a microfluidic substrate 210 that provides both electrical connection to the support electronics and fluidic interconnections between the microanalytical components. The microfluidic substrate 210 can be, for example, an organic laminate printed wiring board (PWB) board, a low-temperature cofired ceramic (LTCC) substrate. Fluidic interconnections can comprise embedded flow channels, such as bypass flow channel 170 and fluidic vias 150 from one side of the microfluidic substrate 210 to the other side and between the component dies that collectively make up the analysis channel. The microfluidic substrate 210 can further comprise a manifold for sample inlet 140 and effluent outlet 190. The microfluidic substrate 210 can further comprises electrical connections (not shown) to a separate PWB board having the support electronics.

Figure 3A:
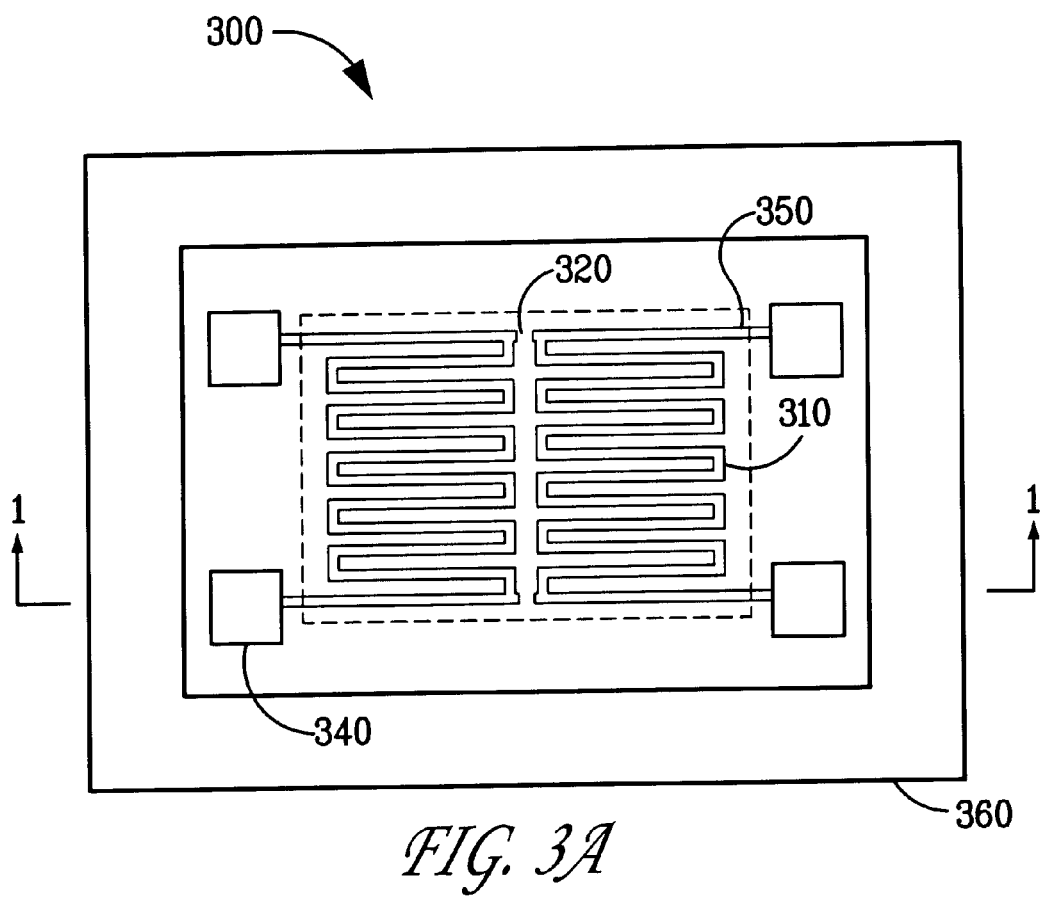
FIG. 3A shows a view of the microfluidic-subtrate-facing side of the preconcentrator die with electrical bond pads formed on the inside of a fluidic seal ring.
Figure 3B:
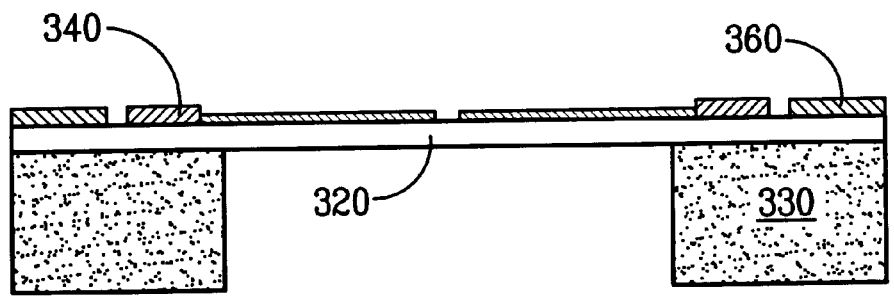
FIG. 3B shows a cross-section view of the preconcentrator die along the line 1—1 in FIG. 3A.

In FIG. 3 is shown a method for making electrical and fluidic connections to a chemical analysis die of a microanalytical component of a hybrid microanalytical system 100. In FIG. 3A is shown a microfluidic-substrate-facing side view of the die 300 for a chemical preconcentrator 110 of the type disclosed in U.S. Pat. No. 6,171,378 to Manginell and Frye-Mason, which is incorporated herein by reference. FIG. 3B shows a cross-section view of the preconcentrator die 300 along the line 1—1. The active electrical element of chemical preconcentrator 110 comprises at least one resistive heating element 310. The resistive heating elements 310 (e.g., platinum) can be disposed on the surface of a thin-film membrane 320 (e.g., silicon nitride) facing the microfluidic substrate 210. The membrane 320 is suspended from an underlying substrate 330 (e.g., silicon). A coating of sorptive material (e.g., a microporous hydrophobic sol-gel coating or a polymer coating, not shown) can be formed on the suspended membrane 320 proximate to the resistive heating element 310 to selectively sorb one or more target analytes from the fluid sample, thereby concentrating the chemical analytes in the sorptive material. The suspended membrane 320 provides for thermal isolation of the resistive heating elements 310 from the substrate 330 to enable rapid desorption of the sorbed chemical analytes to the GC column 120. At least one bond pad 340 can be provided on the portion of the thin film that overlies the substrate 330. The bond pads 340 on the substrate-portion can be electrically connected to the resistive heating elements 310 on the membrane-portion of the thin film by electrical traces 350. A fluidic seal ring 360 can be provided around the outside perimeter of the preconcentrator die 300 to prevent leakage of interferents into and the fluid sample out of the chemical preconcentrator 110.

In the embodiment shown in FIG. 3, the electrical bond pads 340 and the fluidic seal ring 360 can be patterned from the same metallization as the preconcentrator die 300. For example, the bond pads 340 and seal ring 360 can be formed by depositing a 15-nm-thick adhesion layer of titanium and a 100-nm-thick layer of gold on the preconcentrator die 300 through a patterned photoresist mask and using lift-off of the mask. Forming the seal ring 360 around the outside of the resistive heating elements 310 (i.e., the active electrical elements) on the die 300 avoids having to bring the electrical traces 350 out through the seal ring 360. Therefore, with this embodiment, it is not required to electrically insulate the metallized seal ring 360 from the electrical traces 350.

Figure 4:
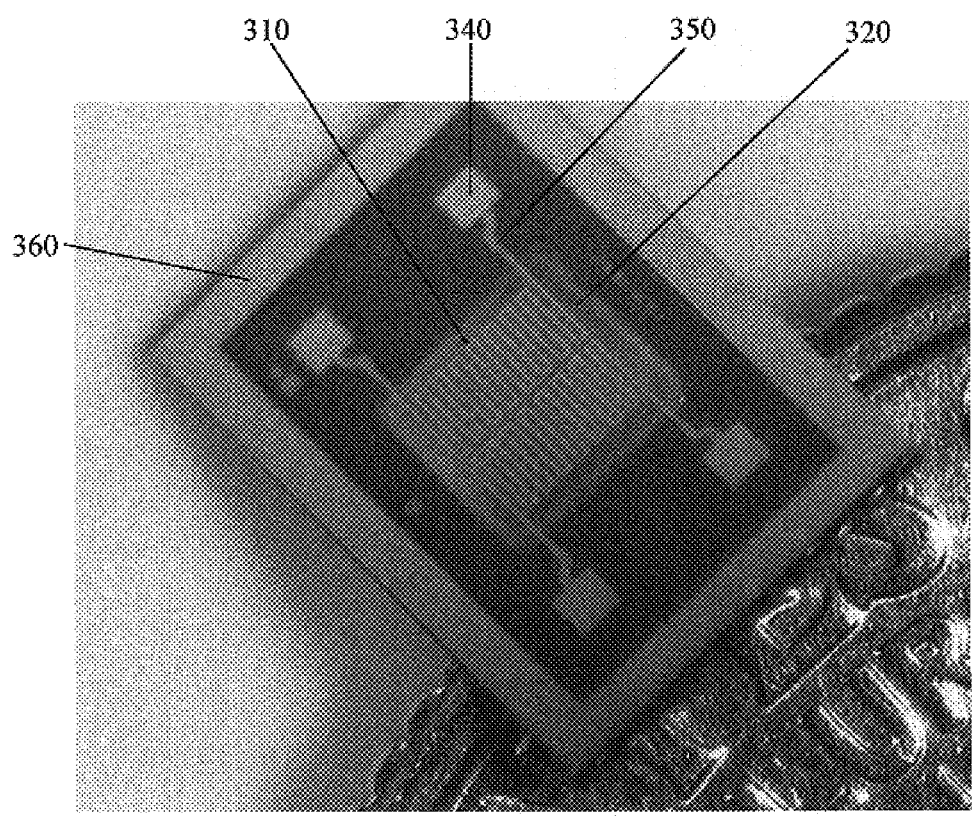
FIG. 4 is a photograph of the preconcentrator die.

FIG. 4 is a photograph of the microfluidic-substrate-facing side of the preconcentrator die 300 comprising two resistive heating elements 310 on suspended membrane 320 and four bond pads 340 within a seal ring 360 around the perimeter of the die 300.

Figure 5A:
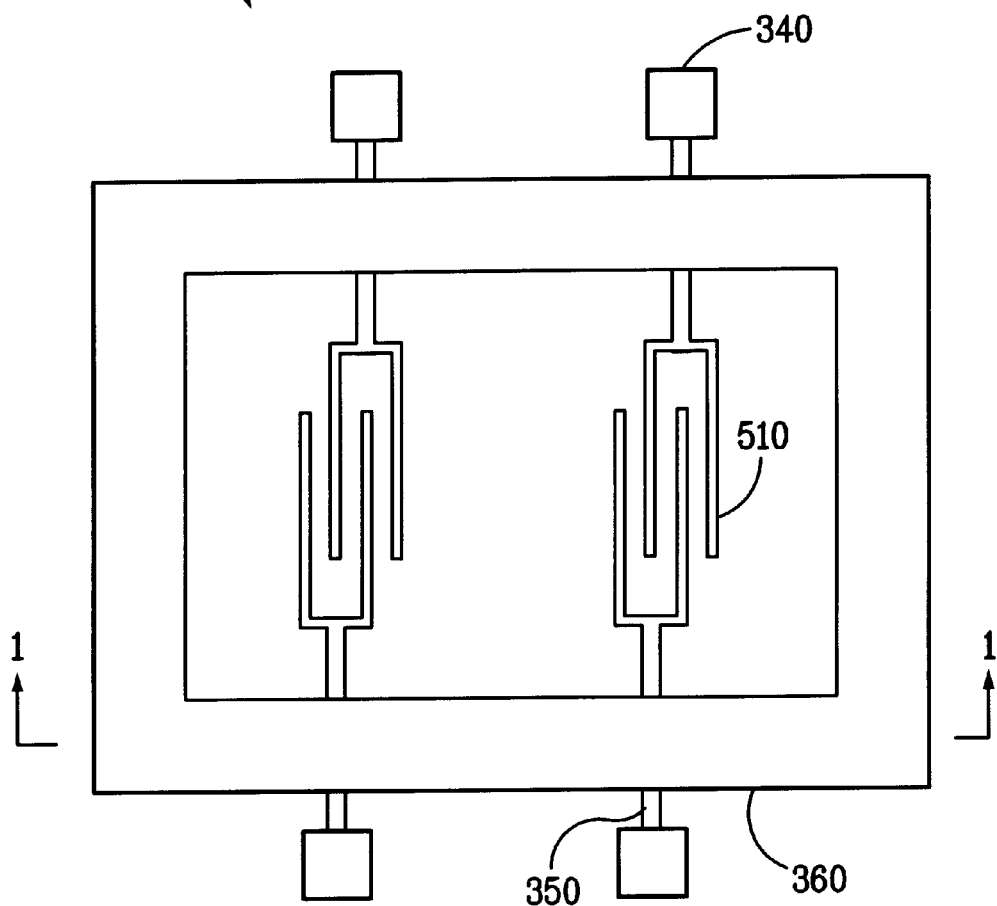
FIG. 5A shows a view of the microfluidic-substrate-facing side of detector die with electrical bond pads formed on the outside of the fluidic seal ring.
Figure 5B:
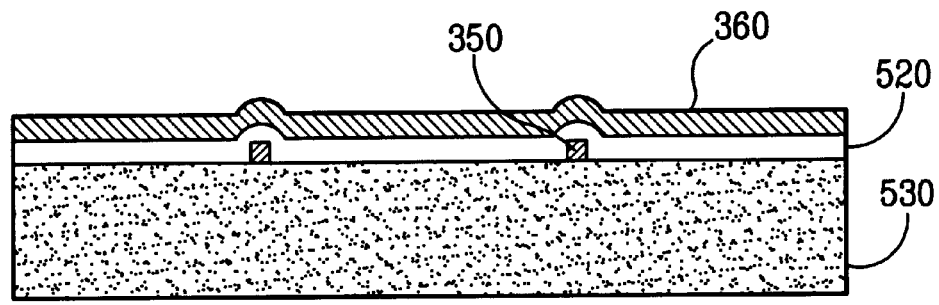
FIG. 5B shows a cross-section view of the detector die along the line 1—1 in FIG. 5B.

Alternatively, the bond pads and electrical connections to the active electrical elements can be formed on the outside of the fluidic seal ring. In FIG. 5 is shown a schematic illustration of a die 500 for a SAW detector 130. FIG. 5A shows a microfluidic-substrate-facing side view of a detector die 500 wherein the bond pads 340 are formed outside of the seal ring 360. FIG. 5B shows a cross-section view of the detector die 500 along the line 1—1. The interdigital transducers 510 (i.e., the active electrical elements) of the SAW detector 130 are formed on the inside of the seal ring 360. As shown in FIG. 5B, in this embodiment the electrical traces 350 connecting the interdigital transducers 510 to the bond pads 340 are run out underneath the seal ring 360. The electrical traces 250 can be first patterned on the substrate 530. A dielectric layer 520 can then be patterned on the die 500 to cover the electrical traces 350. The dielectric layer 520 can preferably be silicon dioxide or silicon nitride deposited by conventional microelectronic methods, with a thickness of about one micron. The metallization for the seal ring 360 can then be patterned on the dielectric layer 520. The seal ring 360 can be a metal layer, such as that used for the bond pads 340, and can be formed simultaneously with the formation of the bond pads 340. Having the bond pads 340 on the outside of the seal ring 360 minimizes the dimensions for the flow channel (i.e., as defined by the seal ring 360), thereby confining the fluid to flow substantially over the interdigital transducers 510 of the SAW detector 130. This arrangement increases the interaction of the separated chemical analytes with the interdigital transducers 510 and reduces the exposure of wetted materials to the fluid.

The chemical analysis die 300 or 500 can be electrically and fluidically connected to the microfluidic substrate 210 in a single step with an electrically conductive sealant, such as solder, conductive epoxy, or Z-axis elastomer. For solder, solder paste can be patterned on the seal ring 360 and bond pads 340 of the chemical analysis die 300 or 500. Alternatively, the solder paste can be patterned on the matched seal ring 670 and the matched bond pads 640 of the microfluidic substrate 210. After the chemical analysis die 300 or 500 is assembled so that the bond pads and seal rings of the die 300 or 500 and the microfluidic substrate 210 are matched, the solder paste can then be heated to melt the solder to form the electrical connections and fluidic seal. To minimize flux contamination, a fluxless solder can be used with a fluorine plasma pretreatment to clean the contact areas prior to bonding. For conductive epoxy, liquid conductive epoxy can be patterned on the chemical analysis die 300 or 500 or on microfluidic substrate 210. Alternatively, pieces of conductive epoxy sheet can be cut out, for example by laser machining, and placed over the bond pads and seal ring on the die 300 or 500 or on the microfluidic substrate 210. The microfluidic-substrate-facing side of the die 300 or 500 can then be placed on top of the microfluidic substrate 210 and mild heat and light pressure can be applied to bond and simultaneously form the electrical and fluidic connections. Alternatively, the sealant can be a Z-axis elastomer sandwiched between the die 300 or 500 and the microfluidic substrate 210 to form an electrical connection between the bond pads and to form a fluidic seal around the fluidic via holes 150 when the chemical analysis die 300 or 500 and the microfluidic substrate 210 are pressed together.

The height of the flow channel is determined by the sum of the thicknesses of the metallizations on the die 300 or 500 and the microfluidic substrate 210 and the final thickness of the sealant. Heights of 0.003" to 0.010" (75–250 $\mu$m) can be easily generated based on typical thicknesses for metallization layers and for solder or epoxy layers. The wetted materials that are exposed to fluid therefore include the sealant, the metal layers, the active electrical element materials, the chemical analysis die material and the microfluidic substrate material.

Figure 6A:
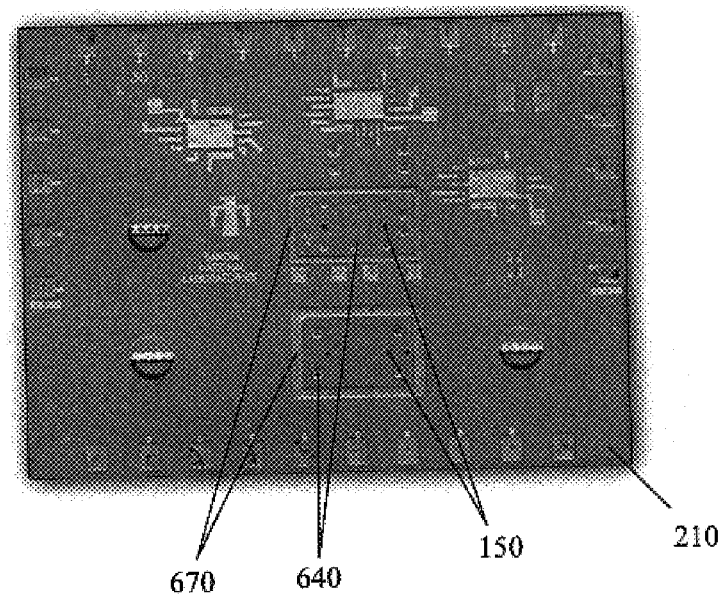
FIG. 6A is a photograph of the LTCC substrate with solder paste patterned on the matching bond pads and matching seal ring.
Figure 6B:
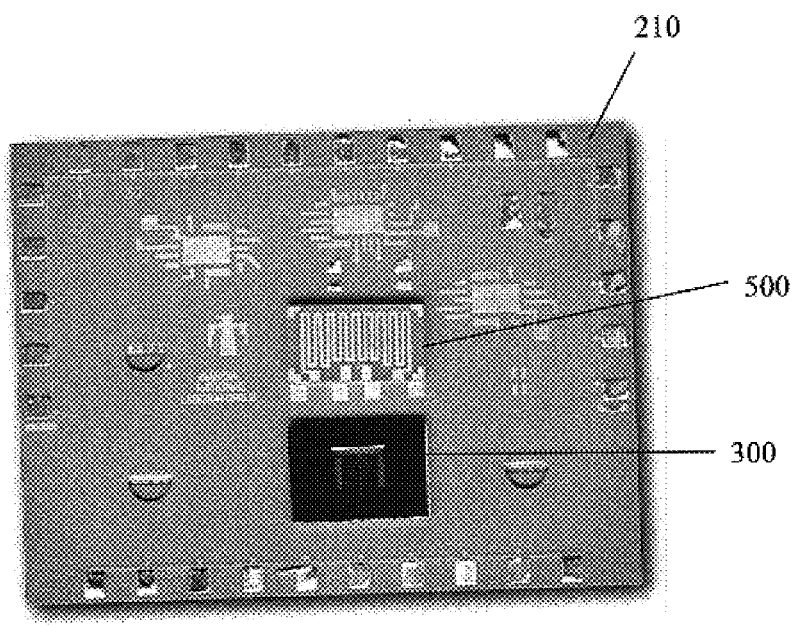
FIG. 6B is a photograph of the LTCC substrate after bonding thereto of a preconcentrator die and a detector die.

In FIG. 6A is shown a photograph of the LTCC substrate 210 prior to assembly and bonding of the chemical analysis die 300 and 500. Four matching electrical bond pads 640 and a matching seal ring 670 are patterned with solder paste for bonding to the preconcentrator die 300. The matching bond pads 640 provide electrical connection of temperature control circuitry (not shown) to the resistive heating elements 310 through the bond pads 340 on the preconcentrator die 300. The seal ring 360 on the preconcentrator die 300 is bonded to the matching seal ring 670 on the LTCC substrate 210 to provide a fluidic seal. Through-via inlet and outlet holes are also provided for fluid flow over the resistive heating elements 310 of the preconcentrator die 300. Similar matching bond pads, seal ring, and fluidic via holes for a SAW detector 130 are also shown. FIG. 6B shows the LTCC substrate 210 after assembly and bonding of the preconcentrator die 300 and the SAW detector die 500.

An alternative method to bond a chemical analysis die to the microfluidic substrate 210 comprises directly bonding the microfluidic substrate 210 to the die 300 or 500 with a non-conductive sealant (e.g., epoxy) to form a fluidic seal ring that circumscribes the active electrical elements and bonding the bond pads 340 of the die 300 or 500 to matching bond pads 640 of the microfluidic substrate 210 with a conductive sealant to form the electrical connection. This arrangement is similar to the arrangement shown in FIG. 5, except that the metallized seal rings 360 and 670 are not required on the die 300 or 500 or on the microfluidic substrate 210. Rather, the fluidic seal is formed by the ring of nonconductive sealant that attaches to the die 300 or 500 and the microfluidic substrate 210 during the direct bonding. This alternative method also allows an insulating seal ring to be formed on the inside of the electrical connections without the step of depositing the dielectric layer 520 otherwise required to provide electrical standoff from the electrical traces 350 from the metallized seal ring 360.

The present invention is described as a method for forming electro-fluidic connections in a microfluidic device. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A method for forming an electro-fluidic connection from a microfluidic substrate to a die having at least one active electrical element thereon, comprising:

forming at least one bond pad on the die that is electrically connected to the at least one active electrical element, forming a seal ring on the die on the outside of the at least one bond pad and the at least one active electrical element, forming at least one matching bond pad on the microfluidic substrate for connection to external support electronics, forming a matching seal ring on the microfluidic substrate on the outside of at least one fluidic via hole, bonding the at least one bond pad to the at least one matching bond pad with a conductive sealant to form electrical connection from the microfluidic substrate to the active electrical element, and bonding the seal ring to the matching seal ring with a sealant to form a fluidic seal around the active electrical element.

2. The method of claim 1, wherein the conductive sealant comprises solder or conductive epoxy.

3. The method of claim 1, wherein the microfluidic substrate comprises a printed wiring board, alumina, or a low-temperature cofired ceramic.

4. The method of claim 1, wherein the die comprises a chemical preconcentrator die, a gas chromatography column die, or a surface acoustic wave detector die.

5. The method of claim 1, wherein the bond pad forming step and the seal ring forming step comprise patterning a metal layer on the die.

6. A method for forming an electro-fluidic connection from a microfluidic substrate to a die having at least one active electrical element thereon, comprising:

forming at least one bond pad on the die that is electrically connected to the at least one active electrical element, forming a dielectric seal ring on the die on the outside of the at least one active electrical element and the inside of the at least one bond pad, forming at least one matching bond pad on the microfluidic substrate for electrical connection to external support electronics, forming a matching seal ring on the microfluidic substrate around the outside of at least one fluidic via hole, bonding the at least one bond pad to the at least one matching bond pad with a conductive sealant to form electrical connection from the microfluidic substrate to the active electrical element, and bonding the dielectric seal ring to the matching seal ring with a sealant to form a fluidic seal around the at least one active electrical element.

7. The method of claim 6, wherein the conductive sealant comprises solder or conductive epoxy.

8. The method of claim 6, wherein the microfluidic substrate comprises a printed wiring board, alumina, or a low-temperature cofired ceramic.

9. The method of claim 6, wherein the die comprises a chemical preconcentrator die, a gas chromatography column die, or a surface acoustic wave detector die.

10. The method of claim 6, wherein the bond pad forming step comprises patterning a metal layer on the die.

11. The method of claim 6, wherein the dielectric seal ring forming step comprises depositing a patterned layer of silicon dioxide or silicon nitride on the die.

12. A method for forming an electro-fluidic connection from a microfluidic substrate to a die having at least one active electrical element thereon, comprising:

forming at least one bond pad on the die that is electrically connected to the at least one active electrical element, forming at least one matching bond pad on the microfluidic substrate for connection to external support electronics, bonding the at least one bond pad to the at least one matching bond pad with a conductive sealant to form electrical connection from the microfluidic substrate to the active electrical element, and bonding the die to the microfluidic substrate with a sealant to form a fluidic seal ring around the outside of the at least one active electrical element on the die and at least one fluidic via hole in the microfluidic substrate.

13. The method of claim 12, wherein the conductive sealant comprises solder or conductive epoxy.

14. The method of claim 12, wherein the microfluidic substrate comprises a printed wiring board, alumina, or a low-temperature cofired ceramic.

15. The method of claim 12, wherein the die comprises a chemical preconcentrator die, a gas chromatography column die, or a surface acoustic wave detector die.

16. The method of claim 12, wherein the bond pad forming step comprises patterning a metal layer on the die.

17. A method for forming an electro-fluidic connection from a microfluidic substrate to a die having at least one active electrical element thereon, comprising:

forming at least one bond pad on the die that is electrically connected to the at least on active electrical element, forming at least one matching bond pad on the microfluidic substrate for connection to external support electronics, and pressing a ring of Z-axis elastomer between the die and the microfluidic substrate to form an electrical connection between the at least one bond pad on the die and the at least one matching bond on the microfluidic substrate and to form a fluidic seal ring around the outside of the at least one active electrical element on the die and the at least one fluidic via hole in the microfluidic substrate.

18. The method of claim 17, wherein the microfluidic substrate comprises a printed wiring board, alumina, or a low-temperature cofired ceramic.

19. The method of claim 17, wherein the die comprises a chemical preconcentrator die, a gas chromatography column die, or a surface acoustic wave detector die.

20. The method of claim 17, wherein the bond pad forming step comprises patterning a metal layer on the die.

* * * * *